United States Patent
Winniczek

(10) Patent No.: US 6,969,619 B1
(45) Date of Patent: Nov. 29, 2005

(54) FULL SPECTRUM ENDPOINT DETECTION

(75) Inventor: Jaroslaw W. Winniczek, Daly City, CA (US)

(73) Assignee: Novellus Systems, Inc., San Jose, CA (US)

(*) Notice: Subject to any disclaimer, the term of this patent is extended or adjusted under 35 U.S.C. 154(b) by 63 days.

(21) Appl. No.: 10/369,085

(22) Filed: Feb. 18, 2003

(51) Int. Cl.[7] .................. H01L 21/00; H01L 21/66; H01L 21/302
(52) U.S. Cl. ..................... 438/9; 438/14; 438/16; 438/17; 438/706; 438/710
(58) Field of Search ............... 438/9, 14, 16, 438/17, 706, 710

(56) References Cited

U.S. PATENT DOCUMENTS

| | | | |
|---|---|---|---|
| 3,437,578 A | 4/1969 | Gibbs et al. ............ 204/230.7 |
| 4,312,732 A | 1/1982 | Degenkolb et al. .... 204/192.33 |
| 4,528,438 A | 7/1985 | Poulsen et al. ........ 219/121.41 |
| 4,615,761 A * | 10/1986 | Tada et al. .................. 216/60 |
| 4,678,545 A | 7/1987 | Galik ........................ 205/50 |
| 4,828,653 A | 5/1989 | Traini et al. ................. 205/96 |
| 4,859,277 A | 8/1989 | Barna et al. ................. 438/7 |
| 5,097,430 A * | 3/1992 | Birang ...................... 356/72 |
| 5,135,636 A | 8/1992 | Yee et al. ................... 205/96 |
| 5,160,402 A | 11/1992 | Cheng ....................... 216/60 |
| 5,270,222 A | 12/1993 | Moslehi ..................... 438/7 |
| 5,308,447 A | 5/1994 | Lewis et al. ................. 216/23 |
| 5,343,412 A | 8/1994 | Birang ...................... 356/72 |
| 5,362,969 A | 11/1994 | Glenn .................... 250/559.18 |
| 5,414,504 A * | 5/1995 | Litvak et al. ................ 356/72 |
| 5,499,733 A | 3/1996 | Litvak ....................... 216/38 |
| 5,552,012 A * | 9/1996 | Morris et al. ............ 156/272.4 |
| 5,620,581 A | 4/1997 | Ang ........................ 205/96 |
| 5,658,423 A | 8/1997 | Angell et al. ................. 438/9 |
| 5,695,660 A | 12/1997 | Litvak ....................... 216/85 |
| 5,738,756 A * | 4/1998 | Liu .......................... 216/60 |
| 5,877,032 A | 3/1999 | Guinn et al. .................. 438/9 |
| 6,001,235 A | 12/1999 | Arken et al. ................ 205/137 |
| 6,027,631 A | 2/2000 | Broadbent ................. 205/137 |
| 6,071,388 A | 6/2000 | Uzoh ....................... 204/287 |
| 6,074,544 A | 6/2000 | Reid et al. ................. 205/157 |

(Continued)

OTHER PUBLICATIONS

43rd Annual Edition "Metal Finishing for Guidebook Directory 1975", Metal Finishing publication, pp. 624-637 (and cover page).

*Primary Examiner*—Nadine G. Norton
*Assistant Examiner*—Lynette T. Umez-Eronini
(74) *Attorney, Agent, or Firm*—DeLio & Peterson, LLC; Peter W. Peterson

(57) ABSTRACT

A method of endpoint detection during plasma processing of a semiconductor wafer comprises processing a semiconductor wafer using a plasma, detecting radiation emission from the plasma during the semiconductor processing, and tracking data points representing changes in spectra of the radiation as a function of time during the semiconductor processing. At any point prior to or during processing a plurality of profiles are provided, each profile representing a different processing condition affecting detection of the desired plasma processing endpoint of the semiconductor wafer. After selecting a desired profile, a first set of parameters are input, representing simplified values for determining when changes in spectra of the radiation indicate that plasma processing of the semiconductor wafer reaches a desired endpoint. The selected profile converts the input first set of parameters into a larger, second set of parameters, and then applies the second set of parameters to an algorithm that converts data points from the spectra of the radiation as a function of time into an endpoint curve. The method then uses the algorithm to track changes in spectra of the radiation as a function of time and determine when plasma processing of the semiconductor wafer reaches a desired endpoint.

19 Claims, 12 Drawing Sheets

U.S. PATENT DOCUMENTS

| | | | |
|---|---|---|---|
| 6,077,405 A | 6/2000 | Biggs et al. | 204/287 |
| 6,153,115 A | 11/2000 | Le et al. | 216/60 |
| 6,190,927 B1 | 2/2001 | Liu | 438/8 |
| 6,306,755 B1 | 10/2001 | Zheng | 438/631 |
| 6,381,000 B1 | 4/2002 | Tsuto | 355/18 |
| 6,426,232 B1 | 7/2002 | Litvak | 438/8 |
| 6,521,080 B2 | 2/2003 | Balasubramhanya et al. | 156/345.24 |

* cited by examiner

FULL SPECTRUM ENDPOINT DETECTION

BACKGROUND OF THE INVENTION

1. Field of the Invention

The present invention relates to semiconductor processing, and more particularly, endpoint detection during semiconductor plasma processing using optical emission spectroscopy.

2. Description of Related Art

Plasma processing is often employed in manufacturing integrated circuits. Plasma processing uses the action of an electrically conductive gas, composed of ionized gas or molecules, to remove unwanted portions of conductive or insulative patterns. It includes plasma cleaning as a removal of photoresist or plasma based etching of thin films or selected portions of layers of materials on semiconductor wafer substrates. Under ideal semiconductor processing conditions, such plasma etching of a film can be accomplished by using the process for a predefined time. However, variations in material thickness and quality, as well as variation in process operating conditions, are typically difficult to control, and make a timing-based system generally infeasible. A simpler approach has been to process for the longest possible time, thereby ensuring that all wafers are processed to completion. This over-processing has its drawbacks. First, wafers with relatively short clearing times will be subject to the processing plasma for a long time and can incur damage or degradation of the layer beneath the one being etched, since this layer generally should not be etched at all. Second, unnecessarily long processing reduces the throughput of the processing tool and uses too much precursors, thereby increasing the cost of processing.

The prior art has also employed chemical analysis to detect the end-of-process (EOP), or endpoint when the film layer has been completely removed. As the plasma process proceeds, there is a change in the chemical constituents in the plasma, corresponding to the removal of the desired film layer. Since the plasma glows, i.e., gives off light, this change in the constituents may be detected by any device that analyzes specific parts of the spectrum. The cheapest method is using a filter that would filter out a specific desired wavelength, and detect that wavelength.

Another alternative is to use a spectrometer which collects all wavelengths at one time and then detects a specific wavelength or combination of wavelengths and performs mathematical processing of those to determine what has occurred. For example, the component being removed is normally dropping in concentration, while the underlying component may be increasing in concentration, if it begins to be removed. One may look at these components separately, or may take a ratio of these two components in the plasma spectra to enhance the signal. Since the spectrograph normally collects all wavelengths, the process is still difficult since one must determine the wavelength(s) on which to concentrate. Some of the software employed for these techniques are exceptionally complicated, and require still greater knowledge of other concepts, and the tracking and manipulation of many parameters. A typical setup for a current state-of-the-art EOP system involves the following steps:

1) Define detector parameters. Typically a detector such as a mutli-channel charged coupled device (CCD) spectrograph, will have at minimum three parameters: i) Exposure time—the time required to expose the CCD to light, also know as integration time, ii) Sample average—the number of exposures averaged together to yield a spectral data set, iii) Sample interval—the time between the transfer of the spectral data set to the processing device. Other parameters may include: gain on the amplifier between the CCD array and the analog-to-digital converter, temperature control of the CCD, a base line offset, and the like.

2) Set spectrum source. Typical endpoint software packages are very general and require the user to input the actual type of detector, and the range of wavelengths to be processed. Some have the potential for multiple sources, including previously collected data.

3) Select spectrum regions. Regions of the spectrum are selected depending on the nature of subsequent analysis. Parts of the spectrum may be selected, such as single peaks, or bands, or segments of the spectrum. These are usually expressed as the average or the sum of the indicated region. These can be designated as $R_1$, $R_2$, $R_3$, ... $R_N$.

4) Define equations. Typical current state-of-the-art (current art) endpoint software requires the construction of an equation from the $R_1$, $R_2$, $R_3$, ... $R_N$. The equation can be a mathematical combination of the $R_1$, $R_2$, $R_3$, $R_N$, which can include addition, subtraction, multiplication, division and higher math functions.

5) Setup full spectrum parameters. If additional treatment of the spectral data is required, which is not covered by the equations, the current art software will have a "special" window for this set up. Usually this will require several parameters. To use these parameters will require extensive knowledge of higher mathematical theory for proper use.

6) Setup endpoint signal analysis parameters. At this point the setup procedure has provided for the generation of a single datum at a give time T. The entire set of these time dependent data can be called the endpoint curve (EPC). Parameters are required to condition the EPC signal. At times the EPC can be noisy and needs to be smoothed, or filtered. A filter parameter needs to be setup. Some EPCs do not have distinct endpoint characteristics. If that is the case then further processing is required. Usually the derivative, or slope, needs to be computed. Most slopes require further smoothing. Often times the signal needs to be normalized at this point normalization parameters need to be specified.

7) Setup endpoint detection parameters. Once the EPC has been conditioned, it then has to be analyzed to determine if endpoint has occurred. Several methods exist for this analysis. The most common is the threshold method, where the EPC as it evolves in time will cross a some predetermined value, either increasing such that it is greater than that value, or decreasing such that it is less than that value. Generally this requires several parameters.

8) Define minimum and maximum process times. The minimum time is the time before which no clearing of any film can occur and the endpoint algorithm will ignore all signals prior to that time. The maximum process time is the time after which no further processing should occur. Generally if the process duration is near this time some sort of error has occurred.

Most current art software applications will have a separate window, display or tab for each of the eight above-mentioned steps. The use of this software application typically entails the reading of a lengthy set of instructions and often, special training such as a class.

In addition to the above complexities, the endpoint algorithm on some existing systems is inadequate for advanced applications such as barrier etch, poly etchback and critical cleans, since some of these processes have small exposed areas of film subject to etch. This results in very small signal changes. It is therefore important to reduce noise, provide for methods ensuring a robust algorithm, and appropriately scale the display such that the process engineer can see the change.

SUMMARY OF THE INVENTION

Bearing in mind the problems and deficiencies of the prior art, it is therefore an object of the present invention to provide an improved method and system for detecting the endpoint or EOP during plasma processing of a workpiece.

It is another object of the present invention to provide a method and system for detecting a plasma-processing endpoint that simplifies the parameters considered by the plasma tool operator.

It is also an object of the present invention to provide a method and system for detecting a plasma-processing endpoint that facilitates use by those not familiar with plasma spectroscopy.

A further object of the invention is to provide an improved algorithm for employing full spectrum analysis.

It is yet another object of the present invention to provide a method of detecting a plasma-processing endpoint that scales the display so that an operator may readily see the change which indicates EOP.

The above and other objects, which will be apparent to those skilled in art, are achieved in the present invention which is directed to a method of endpoint detection during plasma processing of a semiconductor wafer, comprising processing a semiconductor wafer using a plasma, detecting radiation emission from the plasma during the semiconductor processing, and tracking data points representing changes in spectra of the radiation as a function of time during the semiconductor processing. In particular, the method of the present invention provides at any point prior to or during processing a plurality of profiles, each profile representing a different processing condition affecting detection of the desired plasma processing endpoint of the semiconductor wafer. Following selection of a desired profile, the method includes inputting a first set of parameters into the desired profile. The first set of parameters represent simplified values for determining when changes in spectra of the radiation indicate that plasma processing of the semiconductor wafer reaches a desired endpoint. Using the selected profile, the method converts the input first set of parameters into a larger, second set of parameters, and then applies the second set of parameters to an algorithm that converts data points from the spectra of the radiation as a function of time into an endpoint curve. The method then uses the algorithm to track changes in spectra of the radiation as a function of time and determine when plasma processing of the semiconductor wafer reaches a desired endpoint.

The processing conditions represented by the different profiles may include signal-to-noise ratio and data collection rate. The first set of parameters input into the profile may include process time, and the selected profile converts the process time into sampling interval of the data points. The first set of parameters input into the profile may further include relative detection gain setting, so that the selected profile converts the relative detection gain setting into integration time for the data points.

In general, the first set of parameters input into the profile may be selected from the group consisting of endpoint threshold value, endpoint threshold crossing on peak rise, endpoint threshold crossing on peak top, endpoint threshold crossing on peak fall, maximum processing time, endpoint delay time, and relative detection gain setting. The selected profile may convert the first set of parameters into one or more of the following parameters: sampling interval, detector integration time, detector N average, filtering parameter, normalization period, amplitude or derivative, derivative smoothing filter, and threshold integrity period.

Preferably, the algorithm comprises a single equation, embedded in the desired profile, of a full spectrum analysis of the spectra of the radiation emitted from the semiconductor wafer during plasma processing.

In another aspect, the present invention is directed to a program storage device readable by a machine, tangibly embodying a program of instructions executable by the machine to perform method steps for detecting an endpoint during plasma processing of a semiconductor wafer, the method steps comprising:

detecting radiation emission from the plasma during the semiconductor processing;

tracking data points representing changes in spectra of the radiation as a function of time during the semiconductor processing;

providing a plurality of profiles, each profile representing a different processing condition affecting detection of the desired plasma processing endpoint of the semiconductor wafer;

following selection of a desired profile and inputting a first set of parameters into the desired profile, the first set of parameters representing simplified values for determining when changes in spectra of the radiation indicate that plasma processing of the semiconductor wafer reaches a desired endpoint, using the selected profile to convert the input first set of parameters into a larger, second set of parameters;

applying the second set of parameters to an algorithm that converts data points from the spectra of the radiation as a function of time into an endpoint curve; and using the algorithm to track changes in spectra of the radiation as a function of time and determine when plasma processing of the semiconductor wafer reaches a desired endpoint.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

In describing the preferred embodiment of the present invention, reference will be made herein to FIGS. 1–15 of the drawings in which like numerals refer to like features of the invention.

The present invention provides a powerful and easy-to-use endpoint detection system for semiconductor processing. The invention employs software algorithms and an assembly of readily available hardware. The preferred embodiment of this invention measures the intensity of light emitted by a process plasma as a function of wavelength and time, using optical emission spectroscopy (OES). The method of the invention is applicable to any detection method which provides a large number of process relevant data.

The system of the present invention preferably employs a device for detecting light emissions from a process plasma, which is, in the embodiment described herein, an optical emission spectrograph with a charge coupling device (CCD) array. The preferred system also includes a computational device to serve as a platform for analytical software, such as a personal computer with a Windows-based operating system, and a computational engine to analyze the data from the OES device and indicate to the process tool whether endpoint has occurred. The preferred system also includes a process recipe management system that enables the process tool operator to enter parameters which are passed down to the computational engine, and importantly, a series of profiles which enable the reduction of a complex set of parameters to a much easier-to-use set. A small, easy-to-understand set of parameters is converted to a more complex set via each profile, and this complex set is then used by the computational engine. The profile portion of the system facilitates the use of a complex endpoint algorithm by a wide range of operators and engineers with minimum instruction and no knowledge of plasma emission spectroscopy. While these profiles are not recipes, with a given profile the user will have a great deal of flexibility in setting up a recipe for the endpoint. In practicing the invention, it is desirable to keep the number of profiles to a minimum.

Figure 1:
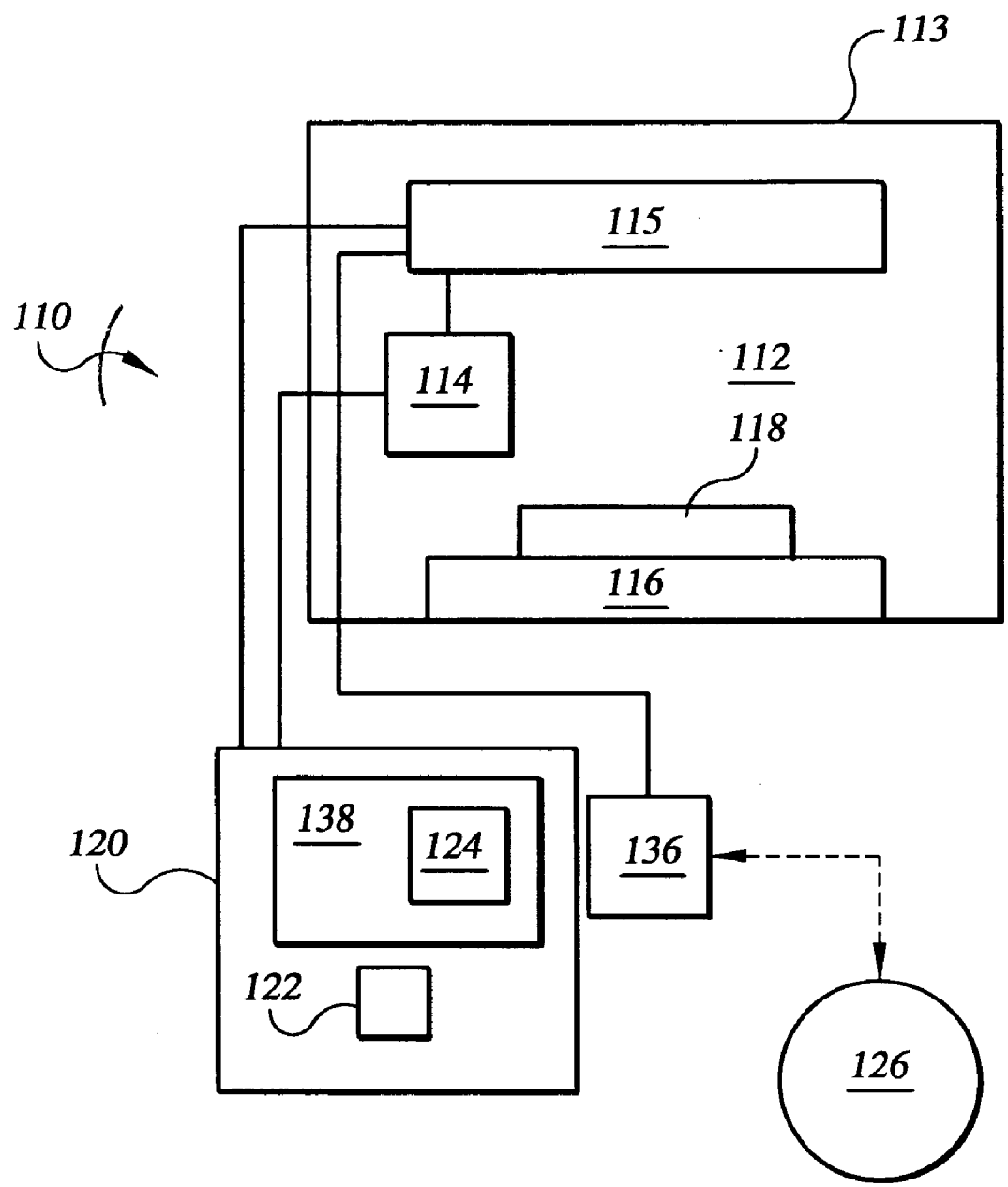
FIG. 1 is a schematic diagram depicting the components of the preferred embodiment of the system for endpoint detection during semiconductor plasma processing using optical emission spectroscopy.

Referring to the schematic diagram in FIG. 1, a preferred embodiment 110 of the components of the present invention is depicted. Plasma processing tool 113 includes chamber 112, an end point detection device which is preferably an optical emission spectroscopy (OES) device 114, and a wafer 118 positioned on a pedestal 116. Alternative devices for detecting light emissions from a process plasma may be used. The preferred optical emission spectrograph 114 includes a CCD array for detecting light. Process control system 115, which is part of the process control module (PCM), controls semiconductor plasma process tool 113 and has display 136 through which the operator 126 communicates with the system.

A computational device serves as a platform for analytical software to determine EOP. In the preferred embodiment 110 shown in FIG. 1, the preferred computational device is a computer system 120 containing a microprocessor 122 and using the same display screen 136, or an optional, different display. Preferably the computer 120 is linked to the OES 114 and is controlled through process tool control system 115 of the semiconductor plasma process tool 113. In the current embodiment, the computer system is preferably a miniature PC running a Windows 2000 or newer operating system, however, alternative computers systems and software can be used by one skilled in the art. The computer system 120 is used to analyze the data from the OES 114 and indicate to the process control system 115 and tool 113 whether endpoint has occurred.

A process recipe management system operated by process tool control system 115 manages the processing of the wafer and enables the process tool operator 126 to enter parameters specified for the process. The recipe is a set of time-sequenced settings of process parameters. This sequence of parameter set points is executed automatically by the process tool control system, or process control module. These parameters are typically flows of feed gases, operating pressures, and electrical power applied to plasma generation sources. The process recipe management system then passes the parameters to the endpoint computational device 120. Rather than rely on the operator to directly input a complex set of parameters into the system, which requires the operator to have a high degree of skill in plasma spectroscopy, the present invention instead stores in the system selection of profiles, which require only a smaller, easier-to-understand set of operational and EOP parameters. The profiles stored in the system are offered to the operator on display 136, who then picks one and enters the smaller set of parameters required.

The preferred endpoint device (EPD), which determines the EOP, is a software algorithm 124 which obtains information from, but is independent of the OES 114. The algorithm 124 operates within computer system 120 and is preferably able to collect, process and store at least 5 data points per second. The EPD can consist of a processor, such as a programmable controller, or an embedded miniature computer. Some of the outlined functions can be performed on the EPD controller or on the process control module. The computer program or software incorporating the process steps and instructions described herein, including the process recipe management, EOP algorithm and profile programs, may be written in otherwise conventional program code and stored on an otherwise conventional program storage device 138, such as a semiconductor chip, a read-only memory, magnetic media such as a diskette or computer hard drive, or optical media such as a CD or DVD ROM.

As the plasma cleaning or removal reaction proceeds, the composition of the material being removed first rises, as the reaction commences, and then falls as the amount of material removed decreases. At some point the concentration of the material removed falls to a low level that may be designated as the EOP. The output of the OES graphs this rise and fall of the concentration of the material removed, represented by the amplitude of the wavelengths of light emitted by the material. This graphical representation is referred to as the endpoint curve (EPC). The EPC can be generated from a variety of signal combinations The OES array detector provides a large number of signals, typically 500 to 2000. These signals need to be reduced to a single endpoint curve, EPC. The EPC is then tested by an algorithm for endpoint. The description herein is directed to an ideal endpoint device, i.e., one utilizing an optical spectrograph.

There are two basic approaches for compressing several hundred data points into a single datum. The first is the traditional, where various sections of the spectrum are summed or averaged; these sums (or averages) can then be combined mathematically to generate the EPC. Typically the sums are over sections of the spectrum which correspond to products, precursors of the process, which are expected to change at endpoint. The other approach is the full spectrum analysis (FSA). FSA does not analyze individual sections of the spectrum, rather it analyzes the entire spectrum to determine how much it has changed over a predetermined period.

The computer system 20 (FIG. 1) reduces a large array of data from the spectrograph, typically 1000 to 2000 pieces of data, to a single quantity which can be interpreted with a straightforward threshold detection algorithm. Algorithm 124, processed by the computer system 120, preferably employs FSA that analyzes variances in spectra, over the entire wavelength range of the spectrograph, as function of time.

The preferred embodiment for FSA is based on the mathematical analysis known as singular value decomposition (SVD). The analysis is conducted on a group of spectra collected at times t–tw to t, where tw is window in time, typically chosen to include 5 to 30 spectra, $\eta(t-tw:t)$. In essence the SVD analysis decomposes the array of spectra, $\eta(t-tw:t)$ into components referred to as factors and vectors. The factors describe the magnitude of variance among the spectra, $\eta(t-tw:t)$, while the vectors describe the nature of the variance. When there are no changes in the spectra over the window, t–tw:t, there will be only a zero-th order factor and vector. If there are no changes in successive spectra through the progress of the semiconductor processing, the array of spectra can be expressed as a single vector and factor. This is true for 5, 10 or even 100 spectra in the window. The SVD formalism ensures that all the vectors are orthogonal. If there are changes in the spectra, higher ordered factors and vectors will emerge. In a steady state situation, as would be expected during etching of a film, or after the film has completely cleared, the constituents of a processing plasma maintain a fixed concentration. Hence, the corresponding spectra as a function of time will be identical. If the steady state is disrupted, such as when the etching of a film approaches completion, then successive spectra will exhibit differences in this transition period.

The zero-th order describes the overall amplitude of the spectra, the vector is a scaled average of the spectra and the overall amplitude is given by the factor. During an etch process there is a steady state concentration of reactive species, i.e. those reaction precursors which will interact with the substrate on the wafer, and products of the etching, i.e. species generated when the reactive species facilitate removal of the substrate by chemically combining with the substrate and desorbing from the surface to the plasma. At endpoint, some species are no longer produced such as byproducts of etch or ash, while others like the precursors increase in concentration because they are no longer consumed. The spectrum will reflect these concentration changes and some spectral peaks will increase while others decrease. At endpoint additional orders of factors and vectors will appear. Typically only the first and second orders are significant. Where as the 0-th order represents global spectral changes, i.e. changes in overall amplitude, the first and second orders represent more local changes or changes where one feature increases while the other decreases.

For endpoint the first order factor is the most useful. The FSA factor at time $T_M$ is referred to as $\eta^1(t)$. This factor is derived from the spectral array, $\upsilon(t-tw:t)$. For most applications it will be a peak, and endpoint is best triggered at the top of the peak or at the right base of the peak.

The first factor $\eta^0(t)$ (0-th order) is proportional to the relative amplitude of the spectra. While the second factor $\eta^1(t)$ shows relative changes. It often looks similar to the derivative of the first factor but is much cleaner and more sensitive to the relative changes. The reason for this is that contributions from noise are placed into the higher order factors. For most cases only the first three orders contain significant information, the higher orders carry the noise.

The designation of the FSA factors within the device specific string (DDS) will be fsa[nw], where n is the order of the factor (0, 1, 2 or 3) while w is the window width (in number of spectra not time). If n is omitted it defaults to 1, and the DDS is written as fsa[w]. For the traditional sum and average under a spectral peak the following notation will be used wsum[$\lambda_1\lambda_2$] and wavrg[$\lambda_1\lambda_2$], where $\lambda_1$ and $\lambda_2$ specify the range of wavelengths for which to construct the sum or the average.

The DDS will have the capability of mathematically combining these three constructs, fsa[nw], wsm[$\lambda_1\lambda_2$] and wavrg[$\lambda_1\lambda_2$]. Mathematical combinations include addition, subtraction, multiplication, division, taking the power, and logarithms. The use of numeric constants should also be available.

A multiplicity of possible endpoint devices may be used in accordance with the present invention. One alternative is a 2 to 4 channel device. In this case a full spectrum analysis (FSA) method will not work, but a DDS may be constructed using notation similar to above: chan1[??], chan2[??], or A[??], B[??] etc. Where the ?? symbolize potential (but not yet conceived) parameters. Of course the fsa, wstum and wavrg notation will not be applicable for this device. The mathematical combinations will be applicable.

Figure 2:
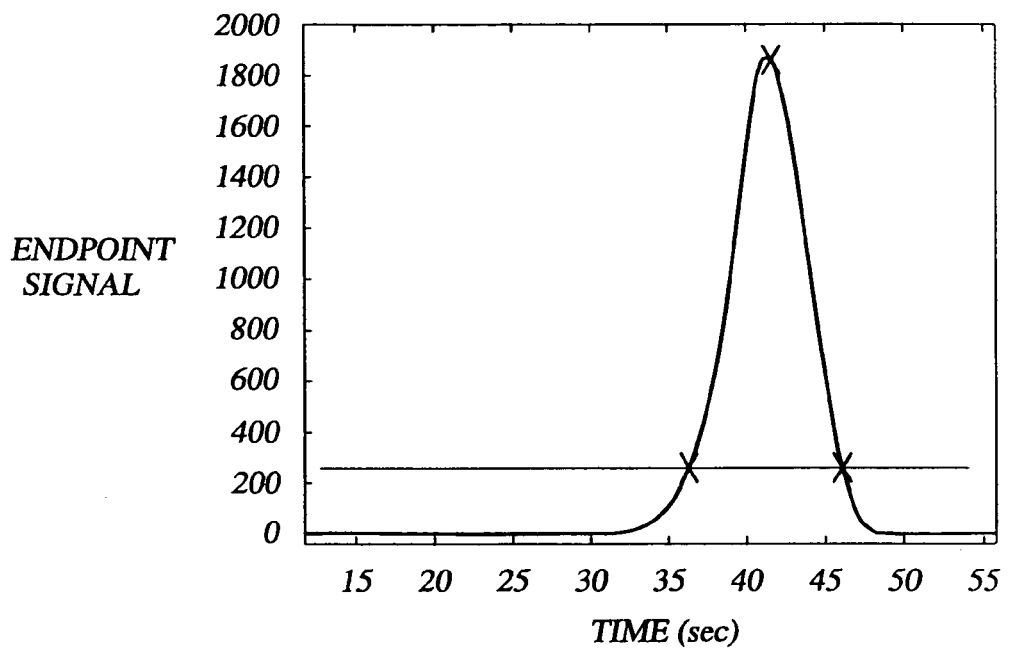
FIG. 2 is a graphical representation of an example of the plot of the first factor of the endpoint in a plasma etch process.
Figure 3:
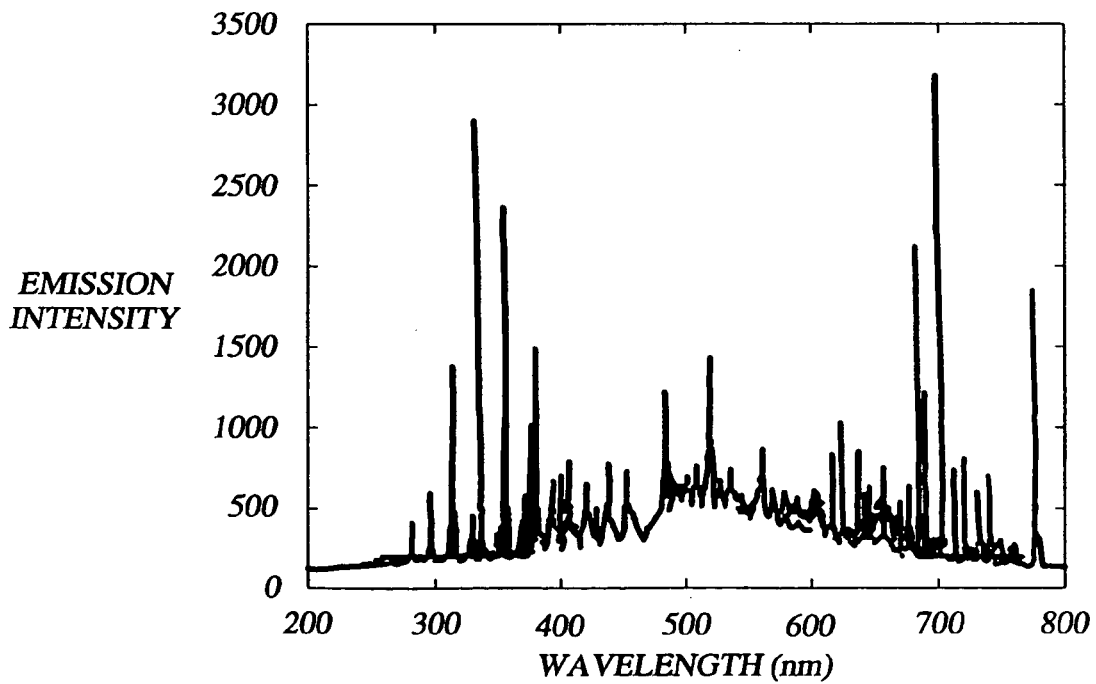
FIG. 3 is a graphical representation showing the spectra required to achieve the plot depicted in FIG. 2.

Referring to FIG. 2, a typical plot is shown of the first order factor of an endpoint for an actual plasma etch process. FIG. 3 shows the spectra required to achieve this plot. The spectra are for the time fragment from 30 to 50 seconds. The utility of employing an algorithm is demonstrated by the fact that the original data set from 30 to 50 seconds contained 40 individual spectra with 2000 points per spectrum. These are reduces to just 40 data points in the plot in FIG. 2.

FIG. 2 also shows a threshold, which permits the triggering of endpoint in three places: 1) as the curve rises above the threshold, 2) as the curve starts falling, after clearing the rising and top portions of the peak, and 3) as the curve falls below the threshold, after first rising above the threshold and hitting a peak.

The generation of the FSA curve need not proceed via the SVD method. Other known mathematical methods for data compression and reduction can be employed. Typically the FSA algorithm produces a smooth curve. The threshold detection algorithm has the feature of filtering data and using a threshold integrity period to ensure that the threshold is really crossed. The advantage of this algorithm is that noise removal, by delegation of noise to higher orders, is a natural consequence of SVD.

Figure 4A:
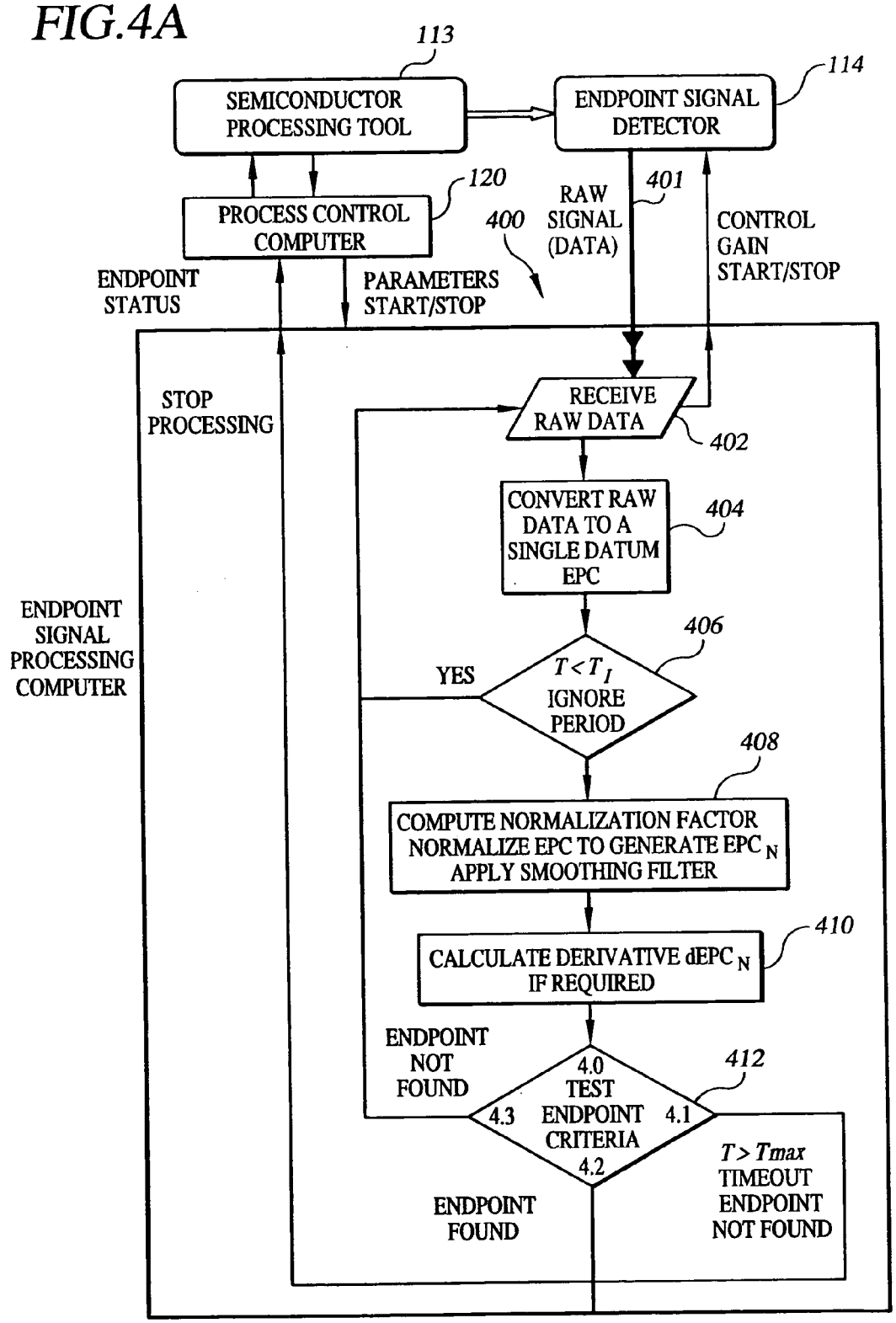
FIGS. 4A and 4B are flowcharts showing the preferred algorithm employed in the present invention for detecting the endpoint during semiconductor plasma processing using optical emission spectroscopy.
Figure 4B:
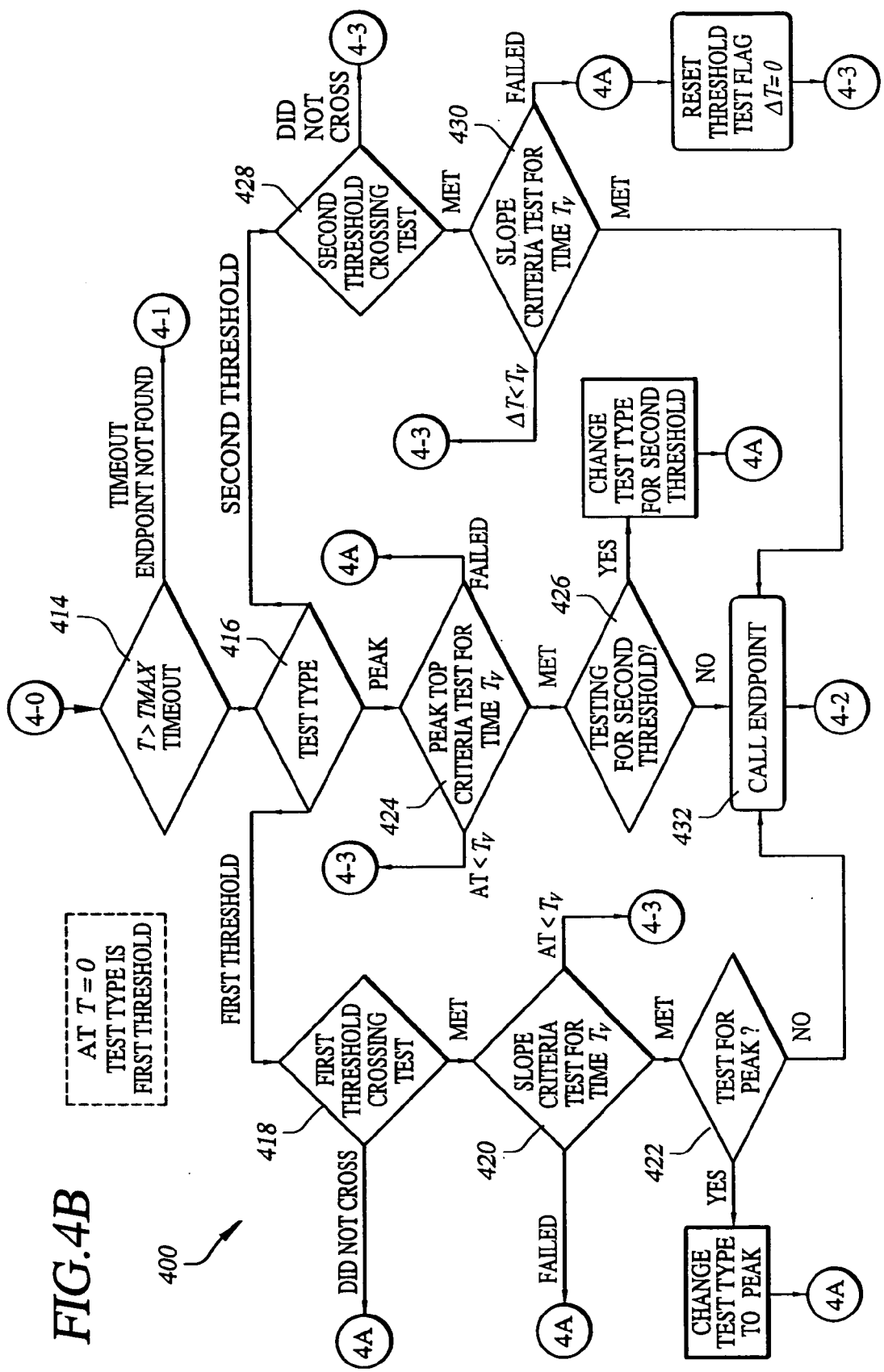

The preferred algorithm 400 is shown in flowchart form in FIGS. 4A and 4B. The algorithm is presented with a signal 401 from the endpoint signal detector, referred to as the endpoint curve, or EPC, and then determines if the EPC has crossed a predetermined threshold. The EPC can cross the threshold as a rising signal, as a falling signal, as a peak, or as a valley. All of these possibilities may be available as parameters to the algorithm. The raw EPC ($EPC_1$) is generated in endpoint device EPD. $EPC_1$ can be a single channel of data, a ratio of two channels of data, a difference or some other more complex signal combination.

FIGS. 4A and 4B are linked by the decision choices 4-0, 4-1, 4-2 and 4-3 in FIG. 4A, which are shown in circles in FIG. 4B. After a semiconductor wafer is positioned in a processing chamber, the algorithm shown in FIGS. 4A and 4B includes the steps below.

1) At the start of each process step send sampling interval v, and gain parameters to the endpoint device, EPD.
2) Receive raw signal 402 from EPD as multiple channels of data, typically spectral data at a time T.
3) Convert the multiple channels of data to a signal datum 404 at time T, $EPC_1$. Typically apply the full spectrum analysis (FSA) algorithm to the data.
4) Ignore further data process 406 for a delay period (or ignore period) $T_1$. If T is less than $T_1$ proceed to step 402.
5) Compute normalization factor 408 during the normalization period $T_N$. If T is less than $T_1+T_N$ proceed to step 402.
6) Normalize $EPC_1$ to $EPC_N$ if called for in the parameter list.
7) Apply smoothing filter $\tau_F$ to convert $EPC_1$ to $EPC_{SM}$. Use the equation S(t)= average [D(t−$\tau_F$:t)], where D(t) is $EPC_1$, and S(t) is $EPC_{SM}$.
8) Depending on the value of $A_OD$, convert $EPC_N$ to its derivative $dEPC_N$, and smooth the derivative using the filter $\tau_s$. This yields the "tested" endpoint curve 410. $EPC_T$.
9) Subject $EPC_T$ to the threshold test 412 depending on the threshold value V, threshold integrity period $T_V$ and threshold direction/type—TDT. If the time T is greater than a predetermined maximum process time, the endpoint is not found and the process is stopped. If the time T is less than the predetermined maximum process time, a test type is selected 416 to determine if the criteria for endpoint are achieved to trigger end of process (EOP) for the current process step. If the criteria are not met return to step 402. The test types are described below:

a) First threshold crossing test 418. This test determines if $EPC_T$ has crossed the threshold, thereby triggering EOP. If the threshold is not crossed, the endpoint is not found, and return to step 402. If the threshold is crossed, continue to slope criteria test 420 to determine if $EPC_T$ has continued to increase (or decrease in the case of a valley) in the same direction for a time $T_V$. The slope test criterion ensures that a spurious threshold crossing does not trigger endpoint. The endpoint curve $EPC_T$ must be above (below for a valley or drop) threshold and maintain a positive slope (negative for valley or drop) for a time $T_V$. An internal time counter is initiated at the first threshold crossing, ΔT. If ΔT is less than $T_V$ the algorithm will need more data and proceed to 4-3. The ΔT criterion will be considered to have failed if the slope changes direction and becomes zero or negative in the time interval ΔT<$T_V$. At this time the counter will be reset and the algorithm will go to 4A (output 4-3 of step 412) and new data will be received 402. Note that ΔT is kept at zero until the threshold is actually crossed for the first time. If this criterion is met, determine whether or not to test for peak as well. If the EOP is to be determined by the first threshold only, the endpoint is then called 432 and, as shown in FIG. 4A, the endpoint is considered found (output 4-2 of step 412) and processing is stopped. If the peak test is to be performed, go to step 424.

b) Peak top test 424. This test determines if $EPC_T$ has passed a peak top or valley bottom, by determining if $EPC_T$ has switched direction and continues to decrease (or increase in the case of a valley) for a time $T_V$. The slope test criterion ensures that a spurious peak does not trigger endpoint. The endpoint curve $EPC_T$ must have changed slope from positive to negative, and maintain a negative slope for a time $T_V$. (Changed slope from negative to positive for valley). The internal time counter ΔT was reset after the fulfillment of the first threshold crossing criteria. If ΔT is less than $T_V$ the algorithm will need more data and proceed to 4-3. The ΔT criterion will be considered to have failed if the slope changes direction and becomes zero or positive in the time interval ΔT<$T_V$. At this time the counter will be reset and the algorithm will go to 4A (output 4-3 of step 412) and new data will be received 402. If this criterion is met, determine whether or not to test for second threshold as well. If the EOP is to be determined by the peak top (or valley bottom), the endpoint is then called 432 and, as shown in FIG. 4A, the endpoint is considered found (output 4-2 of step 412) and processing is stopped. If the second threshold test is to be performed, go to step 428.

c) Second threshold test 428. This test determines if $EPC_T$ has passed the threshold twice, thereby triggering EOP. If the threshold is crossed a second time, continue to slope criteria test 430 to determine if $EPC_T$ has continued to decrease below (or increase above in the case of a valley) the threshold for a time $T_V$. The slope test criterion ensures that a spurious threshold crossing does not trigger endpoint. The endpoint curve $EPC_T$ must have fallen below threshold and maintain a negative slope for a time $T_V$. (Risen above threshold and a positive slope for a valley). An internal time counter is initiated at the successful detection of a peak, ΔT. If ΔT is less than $T_V$ the algorithm will need more data and proceed to 4-3. The ΔT criterion will be considered to have failed if the slope changes direction and becomes zero or negative in the time interval ΔT<$T_V$. At this time the counter will be reset and the algorithm will go to 4A (output 4-3 of step 412) and new data will be received 402. If this criterion is met, the endpoint is then called 432 and, as shown in FIG. 4A, the endpoint is considered found (output 4-2 of step 412) and processing is stopped.

Figure 5A:
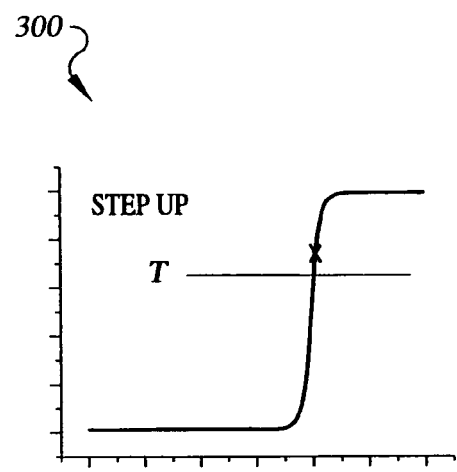
FIGS. 5A–5D are graphical representations of typical endpoint curves during semiconductor plasma processing.
Figure 5B:
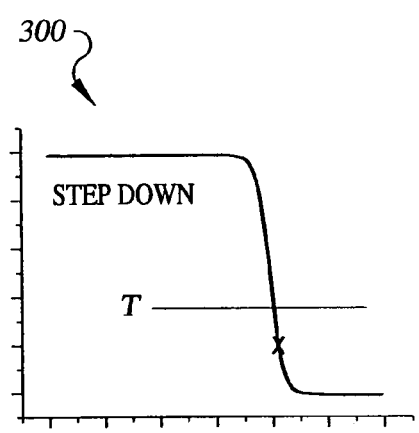
Figure 5C:
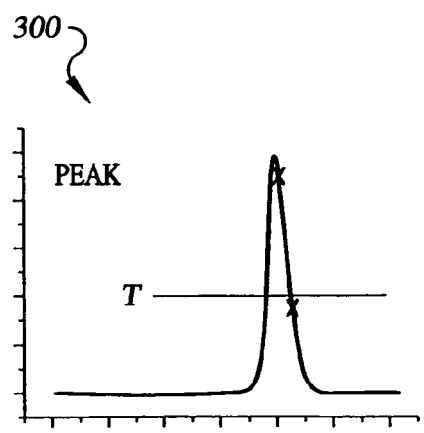
Figure 5D:
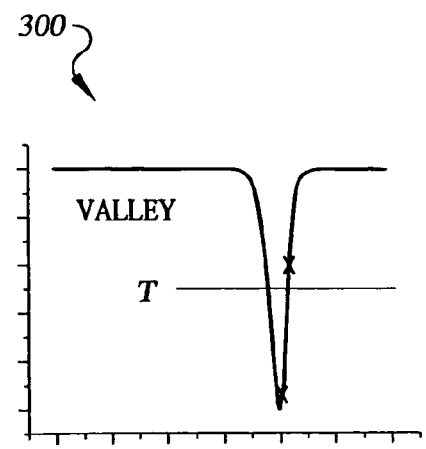

Typical endpoint curves (EPC) are depicted in FIGS. 5A–5D. Such EPC can be given four general shapes with respect to threshold T: 1) a step up, where the signal increases at endpoint, as in FIG. 5A; 2) a step down, where the signal decreases at endpoint, as in FIG. 5B; 3) a peak, where the signal is a maximum at endpoint, as in FIG. 5C;

and 4) a valley, where the signal is a minimum at endpoint, as in FIG. 5D. Threshold trigger T is rather straightforward for the steps in FIGS. 5A and 5B, but is more complicated for the peaks and valleys, as in FIGS. 5C and 5D, since a peak or valley crosses the threshold twice.

Figure 6:
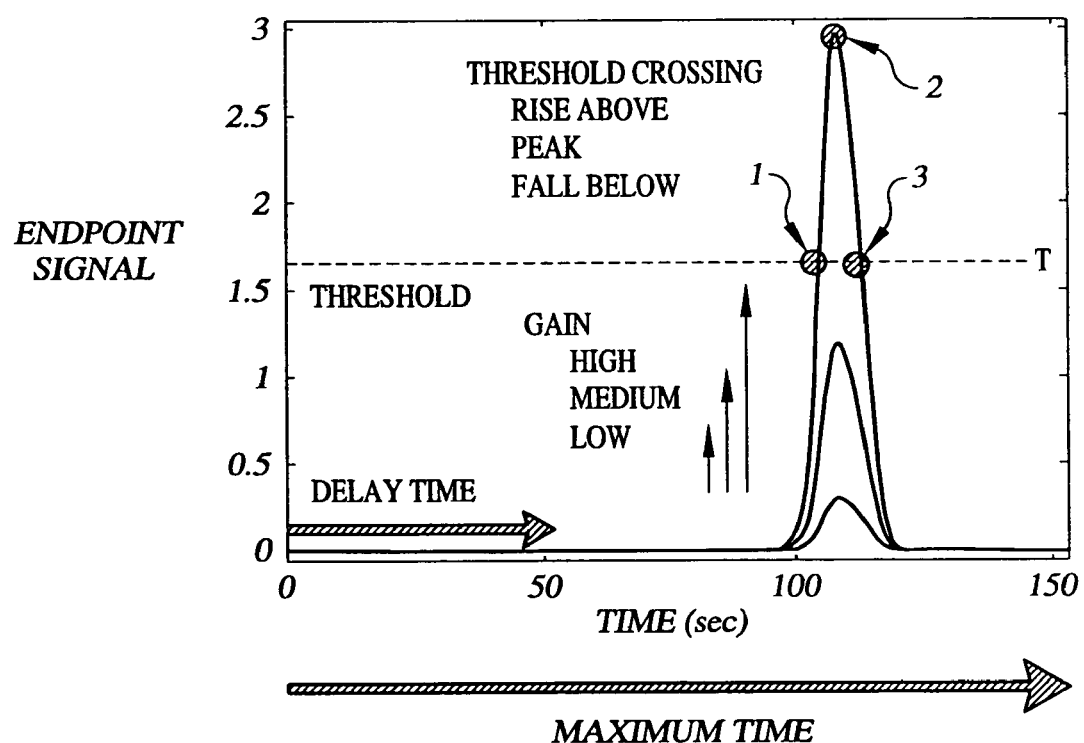
FIG. 6 is a graphical representations of a typical peak endpoint curve.

Another typical peak EPC is shown in FIG. 6. On a peak (or valley) one may wish to trigger endpoint at three locations shown in FIG. 6: 1) initial threshold crossing, which can be handled as a step up (or down for the valley), 2) top of the peak (or bottom of valley), or 3) the second threshold crossing, which can be handled as a step down (or up for the valley), which is similar to the cases in FIGS. 5A and 5B. The preferred algorithm of the present invention handles all six possibilities: 1) step up, 2) step down, 3) peak top, 4) valley bottom, 5) peak base (2nd crossing), 6) valley base (2nd crossing).

Figure 7:
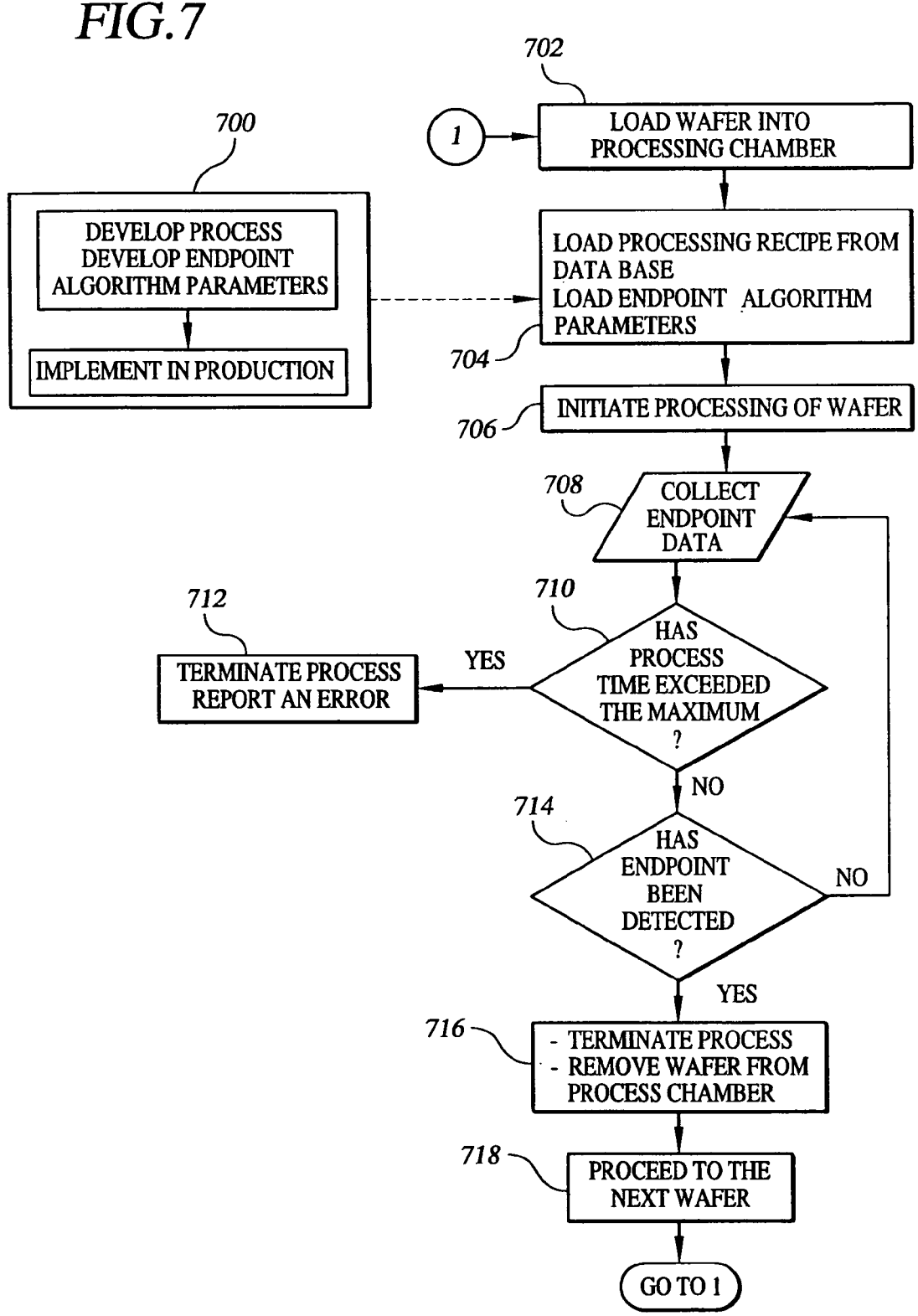
FIG. 7 is a flowchart showing wafer processing, involving a plasma etch, clean or other process, while the endpoint system is engaged and collecting data.

The implementation of a process recipe with endpoint detection, involves the development of a viable plasma etch, clean or other process, as shown in the steps of FIG. 7. Process development 700 entails the adjustment of process parameters, i.e. set-points on the process tool, and measurements of process performance; such that the process results meet production criteria. Typical process parameters include gas flows, pressure, applied power for plasma generation and temperature of substrate. Typical process performance metrics include, etch rates, etch rate uniformities, scanning electron microscope photographs of processed wafer, electrical tests of devices, etc. The development of an endpoint detection scheme usually occurs in the later stages of process development. When the recipe and endpoint algorithm perform according to criteria, they are implemented in production, and loaded into the system 704.

As shown in sequence in FIG. 7, in production a wafer is loaded into a processing chamber 702. It is placed on a pedestal, the chamber is evacuated, gases flows are initiated. When the flows and pressure reach stable conditions power is applied, such as radio frequency or microwave, to generate a plasma. This initiates wafer processing 706. Concurrently with wafer processing the endpoint system is engaged and collects data 708. The processing control system ensures that the processing time does not exceed a maximum time limit 710. If process should exceed the maximum time limit the process is terminated and an error is reported 712. Typical causes for such time-out errors are: 1) loading of improper substrate, 2) a malfunction in the process tool, 3) process recipe and/or endpoint parameters are incompatible with the substrate. The endpoint data are tested for the occurrence of endpoint 714. If the occurrence is detected the process is terminated 716, and if appropriate the next wafer is loaded into the processing chamber 718.

Figure 8:
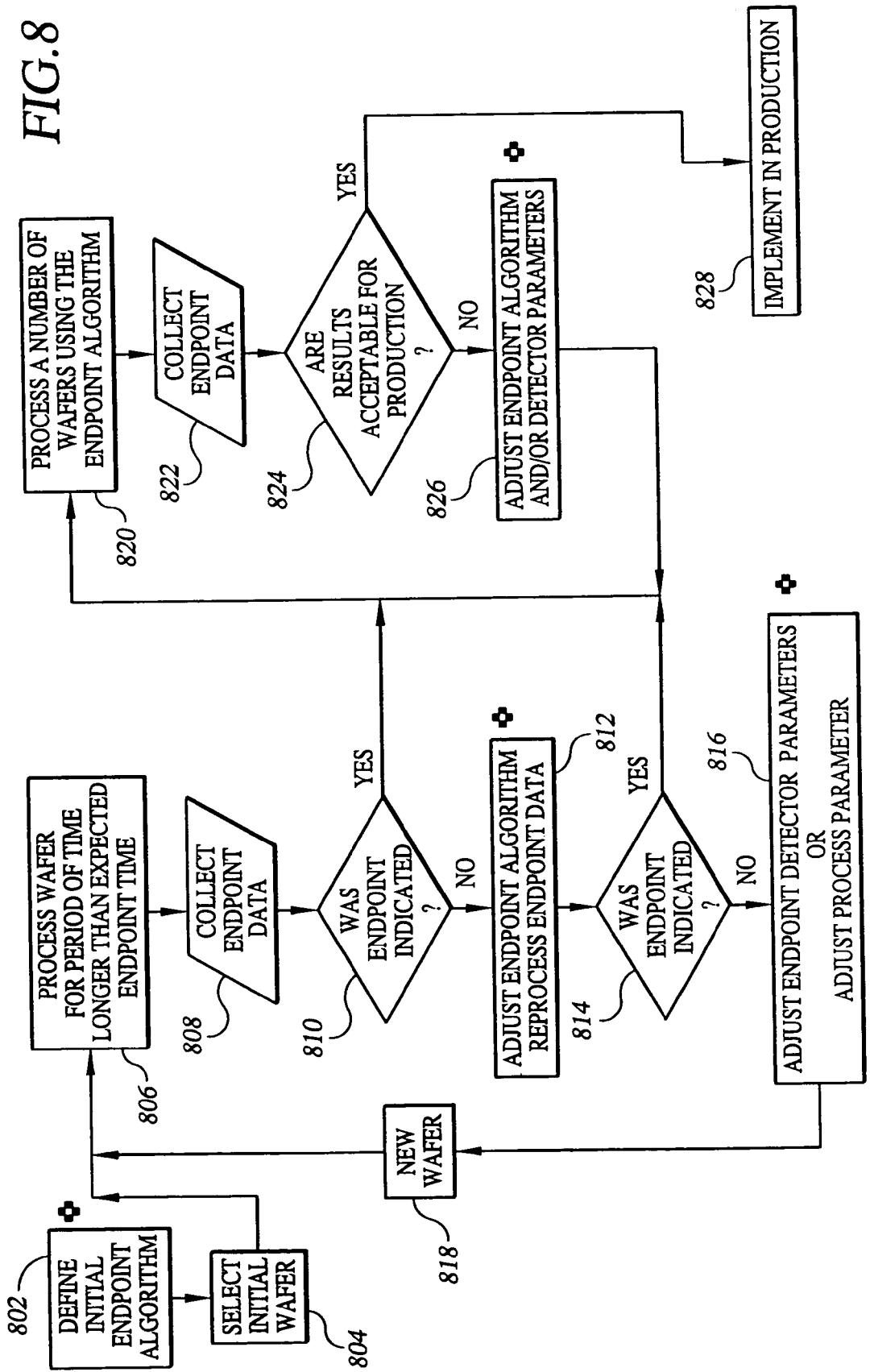
FIG. 8 is a flowchart showing the procedure for selecting an endpoint algorithm and associated parameters.

The procedure for selecting an endpoint algorithm and associated parameters is shown in the flowchart of FIG. 8, and begins with the definition of an initial estimated parameter set 802. At this point the process parameters have been well established and should only be fine tuned in the event that some incompatibility exists between the process and the endpoint algorithm.

The initial endpoint algorithm is tested on the initial wafer 804. This wafer is process for a period of time longer than the expected endpoint time 806. The expected endpoint time should be approximately known on the basis of independent process data, such as etch rates. This extra processing permits the full collection of endpoint data, from the time the film (the substrate being etched) begins to clear to the time the film is completely removed from the entire wafer. Typically the clearing of a substrate is a evolving process, 1) the film thickness over the wafer is not constant, 2) the etch rate has some variability with respect to location on the wafer, 3) the clearing rate changes as the film thickness approaches zero.

The initial endpoint data are analyzed 808 to determine an indication of endpoint 810. If endpoint is found then the algorithm can be tested on several wafers 820. If endpoint is not found then the data can be reprocessed by adjusting the endpoint parameters 812. If this adjustment is successful and the endpoint is indicated 814, then the test can proceed to several wafers 820. If however, the adjustment of endpoint detector parameters 816 is not successful it may be necessary to collect new data with parameters, which are not subject to reprocessing. These include the gain of the detector and the data sample frequency. It may also be necessary to adjust the process 816. In either event, a new wafer is selected and the process is repeated.

Once a successful endpoint parameters set for a single wafer is obtained, it is desirable to test it on a number of wafers 820. This number can vary depending on the application, ranging from 25 to as high as 1000. In this test, a pilot test, the algorithm is set to terminate the process. The aggregate data are analyzed 822 to ensure that endpoint has been found in all cases. A judgment is made 824 to determine if the endpoint algorithm parameters can be transferred to production. The judgment is based on troubleshooting of failed endpoints, ruling out defective wafers. If there are problems then adjustments should be made to the endpoint algorithm and/or detector parameters 826. Otherwise the algorithm can be implemented in production 828.

The definition and adjustment of an endpoint system and algorithm parameter set for production, referenced in steps 802, 812, 816 and 826 in FIG. 8, which is important to effective processing of semiconductor devices, is both simplified and optimized in the present invention. The endpoint algorithm should be robust so as to accommodate inherent variations in material. It also should be sensitive and accurate, to ensure that endpoint is detected on every wafer and at the same point in the progress of the process. In contrast to current systems, the present invention employs a profile program, which permits the selection of a particular profile from a plurality of available profile options by the operator of a semiconductor tool. This provides the operator with the full power of the endpoint algorithm with a minimum learning curve and minimum number of process parameters. In the preferred embodiment, the corresponding software application permits all of the setup to be done in a single window or display.

Figure 9:
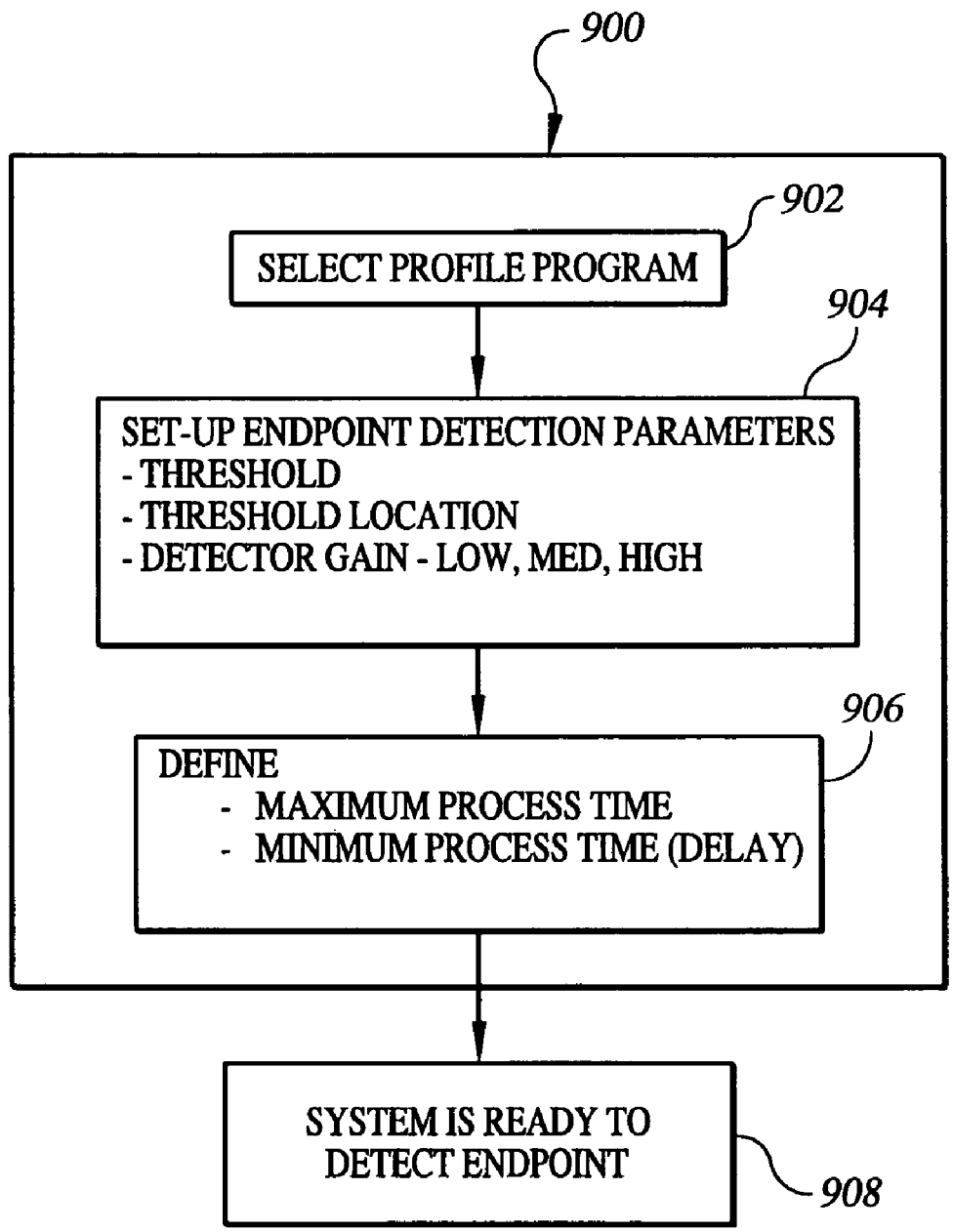
FIG. 9 is a flowchart showing the steps in setting up the endpoint algorithm using the profile in the preferred embodiment of the system for endpoint detection of the present invention.

The steps for the user to follow in setting up the endpoint algorithm using the profile 900 in the preferred embodiment are shown in FIG. 9, and are as follows:

1) Select a profile program 902, from a list of choices which are pre-defined.
2) Set up endpoint detection parameters 904. In one embodiment of this invention the detection parameters will pertain to the threshold method. The threshold parameters include the value of the threshold and its location, as depicted in FIG. 6. The three potential locations of the threshold crossing are 1) Initial crossing where the signal rises above the threshold, 2) change of slope indicative of a peak, and 3) second crossing where the signal falls below the threshold. The algorithm operates as previously described in connection with FIGS. 4A and 4B. In addition the user may selects a simple detector gain, i.e., low, medium or high. The profile program translates this to an actual detector setting.
3) Define minimum and maximum process times 906, as shown in FIG. 6. The minimum time is the time before which no clearing of any film can occur and the endpoint algorithm will ignore all signals prior to that time. The maximum process time is the time after which no further processing should occur. Generally if the process duration is near this time some sort of error has occurred.

The system is them ready to detect the process endpoint 908. In the preferred embodiment, the corresponding software application permits all of the setup, as shown in FIG. 9, to be displayed in a single window or screen (136, FIG. 1) accessed by the operator.

Each of the profile programs operate by transforming a simple set of parameters, as depicted in FIG. 6 to a much larger set, as depicted in FIGS. 4A and 4B. The transformation is dynamic based upon the values of the simple parameter set. The object is to provide a high quality signal, i.e. a high signal-to-noise rate, and to ensure that data are collected at a rate high enough rate to capture the endpoint transition in signal. In the preferred embodiment the maximum process time and detector gain (see FIG. 6) are used to set the sampling interval of the detector and actual gain parameters. The threshold value, threshold location and minimum process time (delay) transfer directly to the full parameter set. The Table below lists the simplified and full parameter sets for a preferred embodiment of this invention

TABLE

| Parameter | Parameter Set Simplified/Full |
|---|---|
| Maximum Process Time - $T_{MAX}$ | S & F |
| Threshold Value - V | S & F |
| Threshold Location - TL | S & F |
| Ignore Period (delay) - $T_I$ | S & F |
| Gain (Low, Medium High) - G | S |
| Sampling Interval - v | F |
| Detector Integration Time - $T_{DI}$ | F |
| Detector N Averages - $N_D$ | F |
| Smoothing Filter - $\tau_F$ | F |
| Normalization Period - $T_N$. | F |
| Normalization Type - NmT | F |
| Amplitude or Derivative - AoD | F |
| Derivative Smoothing Filter - $\tau_S$ | F |
| Threshold Integrity Period - $T_v$ | F |
| Equation - EQ | F |

The mapping scheme between the simplified and full parameter sets is discussed below.

The gain setting G controls the detector integration time $T_{DI}$. A higher gain corresponds to a longer integration time. The longer the integration time is, the better is the signal-to-noise ratio. However, if the intensity of light emitted by the processing plasma is too strong, the detector will saturate to a maximum value, characteristic of the detector. It is therefore necessary to have the ability to control integration time. The simplified gain setting is ideal for this. The profile program converts the simplified gain settings, designated as low, medium or high, to actual integration times.

The process maximum time $T_{MAX}$ is generally selected by the process engineer to ensure that all product wafers will be processed, particularly those which will take longer to clear. Generally $T_{MAX}$ is anywhere from 20% to 50% of the average clearing time (endpoint time). Processes with have longer endpoint times will also have longer clearing periods. The endpoint (clearing) time is the time it takes for the film to clear from the beginning of the process. The clearing period is the time from the onset of clearing, i.e. the film has cleared on a part of the wafer, to the time when all of the film is cleared. It is in this clearing period when the composition of the plasma changes and the corresponding optical emission spectra show change as a function of time. The sampling interval v is adjusted to ensure that enough data is collected during the clearing period. Since there is no way to actually measure the clearing period, a good approximation is where $T_{MAX}$, which is assumed to be reasonably proportional to the clearing period. The interval should be short, such as 0.2 seconds for fast processes where $T_{MAX}$ is less than 30 seconds for example. Conversely, the interval can long, such as 2.0 seconds for slow processes where $T_{MAX}$ is greater than 120 seconds for example. The profile program incorporates a map which adjusts the sampling interval v in accordance to the value of the maximum process time $T_{MAX}$.

Once the sampling interval v and detector integration time $T_{DI}$ are established, it is necessary to set the detector N average ND. This is the number of spectra gathered by the detector at an integration time $T_{DI}$ to average together to output a spectrum to the signal-processing algorithm. Typically sampling intervals range from 0.1 to 5.0 seconds, while detector integration times range from 10 to 500 milliseconds. It is therefore possible to collect anywhere from 1 to 500 spectra within a sampling interval for best signal quality.

The other parameters can be fixed for a give profile program. Alternatively, the filtering parameters, $\tau_F$ and $\tau_S$, can be adjusted with gain G and maximum process time $T_{MAX}$. More filtering can be used for low gain settings, with the assumption that a lower gain signal will have more noise. More filtering can be imposed if the maximum process time is longer, since the signal will most likely exhibit less variation as a function of time. The threshold integrity period Tv can be increased for longer processing times and noisier signals. Longer processing times can also permit longer normalization periods $T_N$.

The selection of amplitude or derivative ($A_oD$) may be a constant within a give profile program, as is the normalization type. The equation EQ is most likely invariant within a given profile program. However, it may be coupled to the gain or maximum process time.

In prior art systems, converting raw signal from a multi-channel source such as a CCD array from a spectrograph, to a single endpoint curve involves many steps, as discussed in the background section. Typically five or more steps are required. The present invention provides a simplified method which reduces these steps to a single equation and significantly simplifies the definition of the profiles. The construction of this equation is typically embedded in the profile program and is not seen by the typical user or operator, who will not be concerned with the equation, but the experienced user acquainted with the art of spectroscopy and endpoint detection will be able to construct new profiles with greater ease.

The equation form will permit arithmetic and transcendental operations, such as addition, subtraction, multiplication, division, exponentiation, logarithms, trigonometric function, etc. The operations will be between single value variables at a give time T. The variables will be constructed from the multi-channel data as a function of time T. In the case of the CCD array spectrograph three possible variable emerge, 1) sum of data under a spectral peak or band, 2) average of data under a spectral peak or band, 3) full spectrum analysis of all data employing as an example SVD (singular value decomposition) of a spectra matrix. The notation for these three cases can be expressed as:

1) wsum[$\lambda_1\ \lambda_2$]

where wsum implies wavelength sum from wavelengths $\lambda_1$ thru $\lambda_2$ 2) wavrg[$\lambda_1$ $\lambda_2$]
   where wavrg implies wavelength average from wavelengths $\lambda_1$ thru $\lambda_2$.
3) fsa[n w]
   where fsa implies full spectrum analysis with a time window width w and an FSA order of n.

The equations can be implemented in either algebraic or reverse polish notation. The following examples demonstrate various possibilities for equations.

wsum[775 779]/wsum[654 658]

log(wsum[775 779]/wsum[654 658])

These equations may be developed by those skilled in the art of plasma processing endpoint detection without undue experimentation.

The different profiles to be prepared and stored for possible use by the process operator preferably accommodate the different signal strengths encountered during processing of different materials and applications. For example, for an application that typically gives off a strong signal, i.e., the strength of the actual signal seen on the spectrometer, the profile program would keep the signal gain low. On the other hand, for an application that typically gives off a weak spectrometer signal, the profile program would employ a greater gain in general, or emphasize a particular part of the spectrum.

Figure 10:
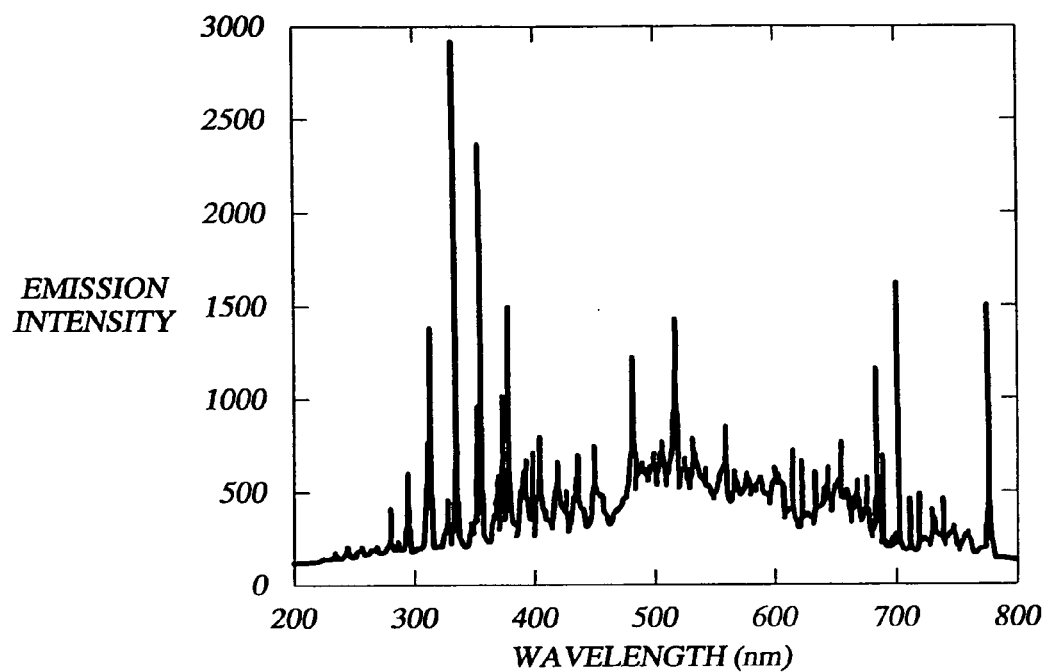
FIG. 10 is a graphical representation of a spectrum of a wafer in a plasma environment undergoing the removal a film layer, before the endpoint has been reached.
Figure 11:
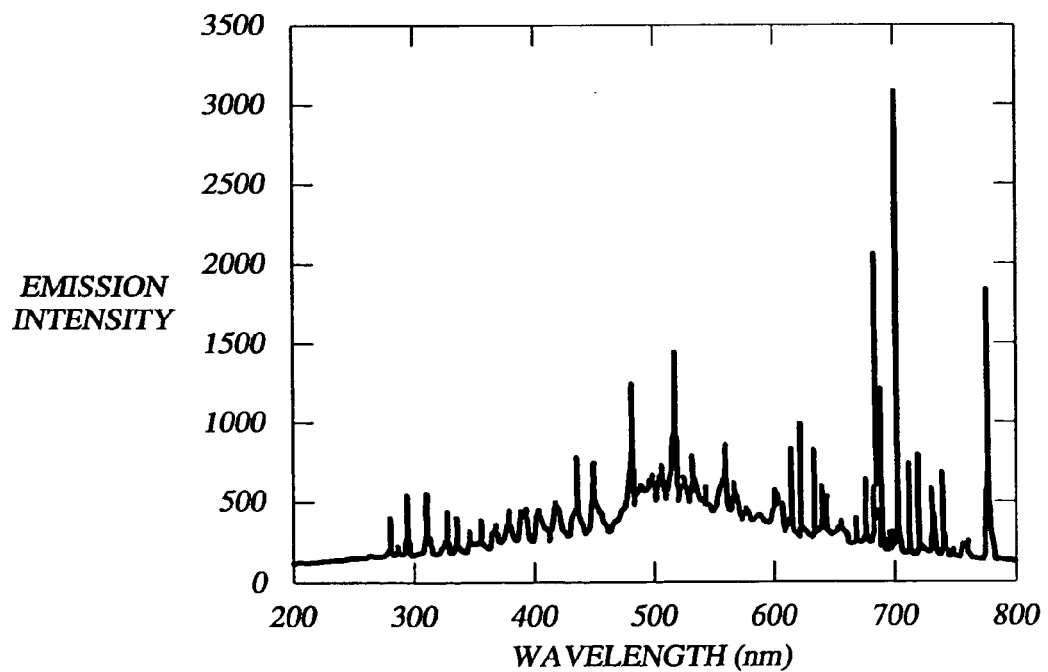
FIG. 11 is a graphical representation of the spectrum of the wafer of FIG. 10 with the layer fully etched, after the endpoint has been reached.
Figure 12:
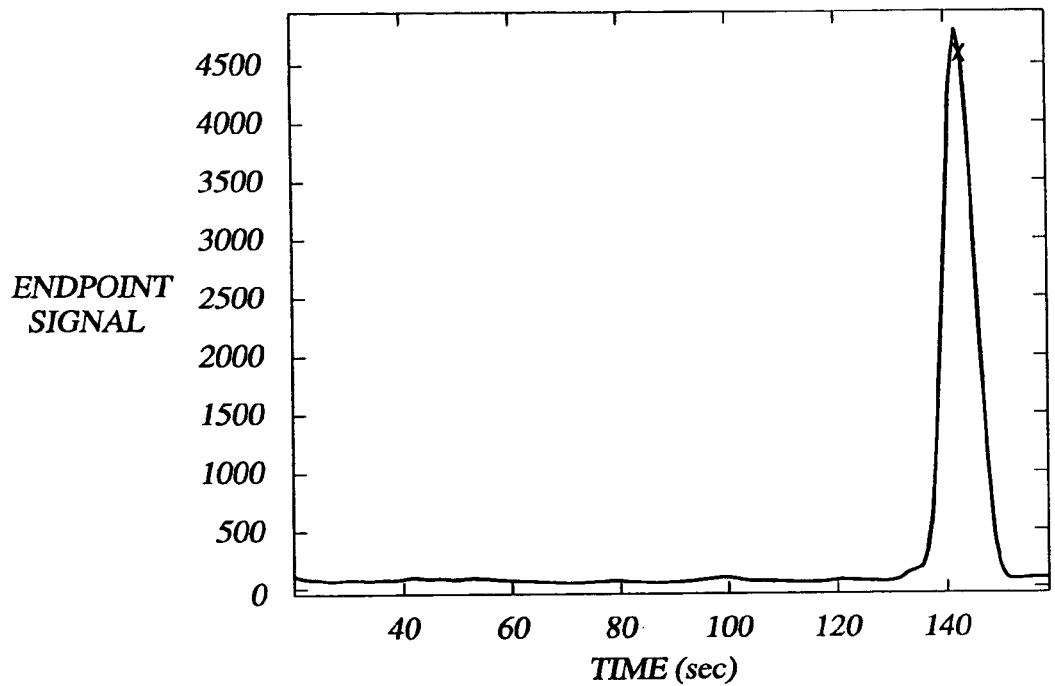
FIG. 12 is a graphical representation of the resulting FSA endpoint curve of the wafer processing depicted in FIGS. 10 and 11.

FIGS. 10 and 11 show a case where a low gain setting can be used to find the endpoint. FIG. 10 shows a spectrum, obtained using a CCD array spectrograph, of a wafer in a plasma environment undergoing the removal a film layer. FIG. 11 shows the spectrum of the same wafer with the layer fully etched. The spectra of FIGS. 10 and 11 are respectively before and after endpoint has been reached. The changes in these spectra before and after endpoint are very distinct, and many spectral features change in amplitude. The resulting FSA endpoint curve is depicted in FIG. 12, a very distinct and sharp indication of endpoint.

Figure 13:
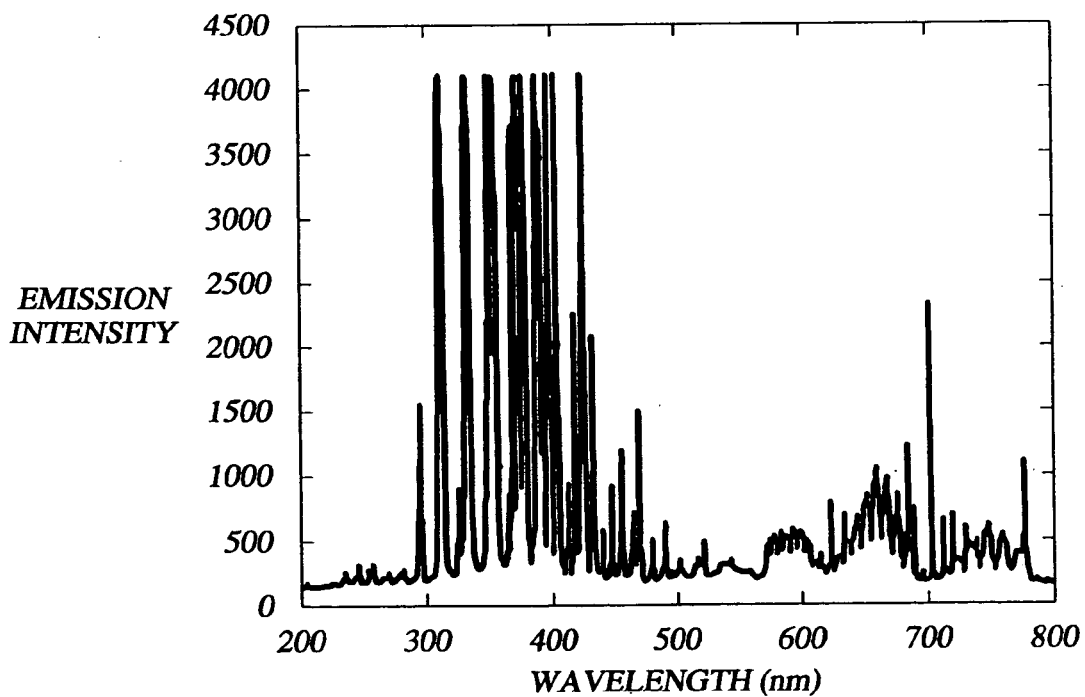
FIG. 13 is another graphical representation of a spectrum of a wafer in a plasma environment undergoing the removal a film layer, before the endpoint has been reached.
Figure 14:
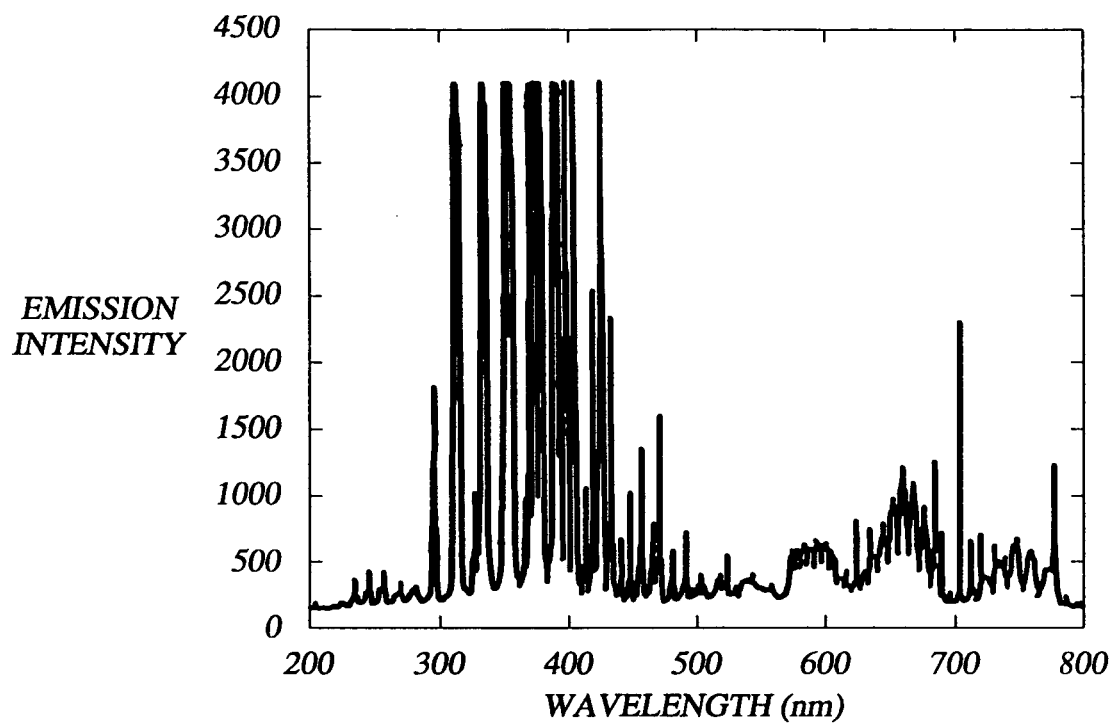
FIG. 14 is a graphical representation of the spectrum of the wafer of FIG. 13 with the layer fully etched, after the endpoint has been reached.
Figure 15:
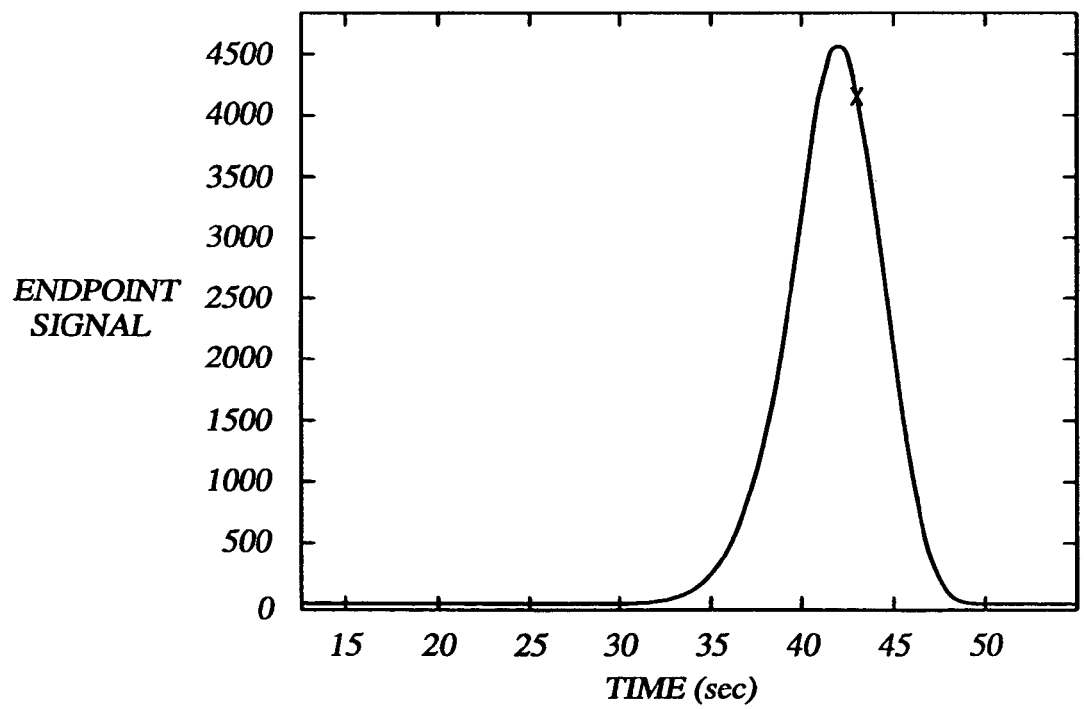
FIG. 15 is a graphical representation of the resulting FSA endpoint curve of the wafer processing depicted in FIGS. 13 and 14.

Conversely, FIGS. 13 and 14 show a case where a high gain setting should be used to find endpoint. Low gain setting will not yield an adequate endpoint curve using the full spectrum method, or any method for that matter. FIG. 13 shows a spectrum, obtained using a CCD array spectrograph, of a wafer in a plasma environment undergoing the removal a film layer, and FIG. 14 shows the spectrum of the same wafer with the layer fully etched. The spectra of FIGS. 13 and 14 are respectively before and after endpoint has been reached. However, the spectra look virtually identical and the changes before and after endpoint are visually imperceptible. Most of the spectral features which define the endpoint are found in the range of 500 to 800 nm. However the strongest features are found in the range 300 to 450 nm. In this particular example the strong but irrelevant features were saturated, such that the signal exceeded the maximum output value of the CCD pixels, in order to enhance the features in the relevant range. The resulting FSA endpoint curve is depicted in FIG. 15, which shows a very distinct and sharp indication of endpoint. This sharp and distinctive curve would not have been possible with a low gain setting. The gain for this example in FIGS. 13–15 is about 20 times larger than for the first example depicted in FIGS. 10–12.

The profiles to be selected by the process engineer or operator are stored in the process control computer (FIG. 1) and may be provided to the process engineer at the beginning or at any point prior to the EOP. The use of predetermined profiles, one of which is to be used in a given plasma process, facilitates the use of a complex endpoint algorithm by a wide range of operators and engineers with minimum instruction and no knowledge of plasma emission spectroscopy. It is preferred that the number of profiles is kept to a minimum, to reduce the complexity of searching for an optimum endpoint recipe. A series of preferred profiles enable the reduction of a complex set of parameters to a much easier-to-use set. With a given profile the users still have flexibility in setting up a recipe that employs full spectrum analysis with endpoints indicating EOP that are readily observable by the operator.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of endpoint detection during plasma processing of a semiconductor wafer, comprising:
   processing a semiconductor wafer using a plasma;
   detecting radiation emission from the plasma during the semiconductor processing;
   tracking data points representing changes in spectra of the radiation as a function of time during the semiconductor processing;
   providing at any point prior to or during processing a plurality of profile programs, each profile program representing a different processing condition affecting detection of a plasma processing endpoint of the semiconductor wafer;
   selecting a profile program;
   inputting a first set of parameters into the selected profile program, the first set of parameters representing simplified values for determining when changes in spectra of the radiation indicate that plasma processing of the semiconductor wafer reaches an endpoint;
   using the selected profile program, converting the input first set of parameters into a larger, second set of parameters;
   applying the second set of parameters to an algorithm that converts data points from the spectra of the radiation as a function of time into an endpoint curve; and
   using the algorithm to track changes in spectra of the radiation as a function of time and determine when plasma processing of the semiconductor wafer reaches an endpoint.

2. The method according to claim 1 wherein the processing conditions represented by the profile programs include signal-to-noise ratio and data collection rate.

3. The method according to claim 1 wherein the first set of parameters input into the profile program includes process time, and wherein the selected profile program converts the process time into sampling interval of the data points.

4. The method according to claim 1 wherein the first set of parameters input into the profile program is selected from the group consisting of endpoint threshold value, endpoint threshold crossing on peak rise, endpoint threshold crossing on peak top, endpoint threshold crossing on peak fall, maximum processing time, endpoint delay time, and relative detection gain setting.

5. The method according to claim 1 wherein the selected profile program converts the first set of parameters into one or more of the following parameters: sampling interval, detector integration time, detector N average, filtering parameter, normalization period, amplitude or derivative, derivative smoothing filter, and threshold integrity period.

6. The method according to claim 1 wherein the algorithm comprises a single equation.

7. The method according to claim 6 wherein the algorithm is embedded in the selected profile program.

8. The method according to claim 1 wherein the algorithm comprises a full spectrum analysis of the spectra of the radiation emitted from the semiconductor wafer during plasma processing.

9. A method of endpoint detection during plasma processing of a semiconductor wafer, comprising:
   processing a semiconductor wafer using a plasma;
   detecting radiation emission from the plasma during the semiconductor processing;
   tracking data points representing changes in spectra of the radiation as a function of time during the semiconductor processing;
   providing a plurality of profile programs, each profile program representing a different processing condition affecting detection of a plasma processing endpoint of the semiconductor wafer;
   selecting a profile program;
   inputting a first set of parameters, including process time, into the selected profile program, the first set of parameters representing simplified values for determining when changes in spectra of the radiation indicate that plasma processing of the semiconductor wafer reaches an endpoint;
   using the selected profile program, converting the input first set of parameters into a larger, second set of parameters, including converting the process time into sampling interval of the data points;
   applying the second set of parameters to an algorithm comprising a full spectrum analysis of the spectra of the radiation emitted from the semiconductor wafer during plasma processing, the algorithm converting data points from the spectra of the radiation as a function of time into an endpoint curve; and
   using the algorithm to track changes in spectra of the radiation as a function of time and determine when plasma processing of the semiconductor wafer reaches an endpoint.

10. The method according to claim 9 wherein the processing conditions represented by the profile programs include signal-to-noise ratio and data collection rate.

11. The method according to claim 9 wherein the first set of parameters input into the profile program further includes parameters selected from the group consisting of endpoint threshold value, endpoint threshold crossing on peak rise, endpoint threshold crossing on peak top, endpoint threshold crossing on peak fall, maximum processing time, endpoint delay time, and relative detection gain setting.

12. The method according to claim 9 wherein the selected profile program converts the first set of parameters into one or more of the following parameters: sampling interval, detector integration time, detector N average, filtering parameter, normalization period, amplitude or derivative, derivative smoothing filter, and threshold integrity period.

13. The method according to claim 6 wherein the algorithm is embedded in the selected profile program.

14. A method of endpoint detection during plasma processing of a semiconductor wafer, comprising:
   processing a semiconductor wafer using a plasma;
   detecting radiation emission from the plasma during the semiconductor processing;
   tracking data points representing changes in spectra of the radiation as a function of time during the semiconductor processing;
   providing a plurality of profiles, each profile representing a different processing condition affecting detection of a plasma processing endpoint of the semiconductor wafer;
   selecting a profile;
   inputting a first set of parameters, including relative detection gain setting, into the selected profile, the first set of parameters representing simplified values for determining when changes in spectra of the radiation indicate that plasma processing of the semiconductor wafer reaches an endpoint;
   using the selected profile, converting the input first set of parameters into a larger, second set of parameters, including converting the relative detection gain setting into integration time for the data points;
   applying the second set of parameters to an algorithm comprising a full spectrum analysis of the spectra of the radiation emitted from the semiconductor wafer during plasma processing, the algorithm converting data points from the spectra of the radiation as a function of time into an endpoint curve; and
   using the algorithm to track changes in spectra of the radiation as a function of time and determine when plasma processing of the semiconductor wafer reaches an end point.

15. The method according to claim 14 wherein the processing conditions represented by the profiles include signal-to-noise ratio and data collection rate.

16. The method according to claim 14 wherein the first set of parameters input into the profile further includes parameters selected from the group consisting of endpoint threshold value, endpoint threshold crossing on peak rise, endpoint threshold crossing on peak top, endpoint threshold crossing on peak fall, maximum processing time, endpoint delay time, and relative detection gain setting.

17. The method according to claim 14 wherein the selected profile converts the first set of parameters into one or more of the following parameters: sampling interval, detector integration time, detector N average, filtering parameter, normalization period, amplitude or derivative, derivative smoothing filter, and threshold integrity period.

18. The method according to claim 14 wherein the algorithm is embedded in the selected profile.

19. A method of endpoint detection during plasma processing of a semiconductor wafer, comprising:
   processing a semiconductor wafer using a plasma;
   detecting radiation emission from the plasma during the semiconductor processing;
   tracking data points representing changes in spectra of the radiation as a function of time during the semiconductor processing;
   providing at any point prior to or during processing a plurality of profiles, each profile representing a different processing condition affecting detection of a plasma processing endpoint of the semiconductor wafer;
   selecting a profile;
   inputting a first set of parameters into the selected profile, the first set of parameters representing simplified values for determining when changes in spectra of the radiation indicate that plasma processing of the semiconductor wafer reaches an endpoint, and including relative detection gain setting;
   using the selected profile, converting the input first set of parameters into a larger, second set of parameters, including converting the relative detection gain setting into integration time for the data points;

applying the second set of parameters to an algorithm that converts data points from the spectra of the radiation as a function of time into an endpoint curve; and using the algorithm to track changes in spectra of the radiation as a function of time and determine when plasma processing of the semiconductor wafer reaches an endpoint.

\* \* \* \* \*